United States Patent [19]

Zeipel

[11] Patent Number: 4,652,712
[45] Date of Patent: Mar. 24, 1987

[54] MICROWAVE APPLIANCE USED FOR WARMING BLOOD OR BLOOD DERIVATIVES STORED IN A BAG

[76] Inventor: Kurt Zeipel, Spandauer Str. 9, 3406 Bovenden-Lenglern, Fed. Rep. of Germany

[21] Appl. No.: 817,148

[22] Filed: Jan. 8, 1986

[30] Foreign Application Priority Data

Jan. 23, 1985 [DE] Fed. Rep. of Germany ....... 3502095
Dec. 7, 1985 [DE] Fed. Rep. of Germany ....... 3543308

[51] Int. Cl.⁴ .............................................. H05B 6/78
[52] U.S. Cl. ...................... 219/10.55 F; 219/10.55 R; 366/232; 366/237
[58] Field of Search ................... 219/10.55 F, 10.55 E, 219/10.55 A, 10.55 R, 10.55 B, 389; 366/232, 237, 238, 239, 240; 604/403

[56] References Cited

U.S. PATENT DOCUMENTS

| 3,427,422 | 2/1969 | Muller ........................... 219/10.55 R |
| 3,777,095 | 12/1973 | Muranaka ..................... 219/10.55 A |
| 4,286,133 | 8/1981 | Einset et al. ................... 219/10.55 E |
| 4,471,193 | 9/1984 | Walter ........................... 219/10.55 F |
| 4,503,307 | 3/1985 | Campbell et al. ............. 219/10.55 E |
| 4,571,474 | 2/1986 | Pomroy ......................... 219/10.55 F |

FOREIGN PATENT DOCUMENTS 2320440 4/1973 Fed. Rep. of Germany .
2418155 4/1974 Fed. Rep. of Germany .

OTHER PUBLICATIONS

W. German patent application No. 7411160.

Primary Examiner—Philip H. Leung
Attorney, Agent, or Firm—Thomas & Kennedy

[57] ABSTRACT

A microwave appliance serving to warm blood or blood derivatives stored in a bag possesses a microwave generator and a receiving apparatus, provided in the warming chamber, for a bag (8). This axis (26) of the bag (8) is arranged transversely to the axis of rotation (4) of a reversibly controlled electric motor. The axis (26) of the receiving apparatus is, in this design, arranged obliquely to the axis of rotation (4) of the electric motor (5). The receiving apparatus possesses a clamping plate (6) for receiving the bag (8).

8 Claims, 4 Drawing Figures

MICROWAVE APPLIANCE USED FOR WARMING BLOOD OR BLOOD DERIVATIVES STORED IN A BAG

FIELD OF THE INVENTION

The invention relates to a microwave appliance having a microwave generator and a warming chamber with a receiving apparatus for a bag which is used for warming blood or blood derivatives stored in the bag.

It is known that preserved blood can be stored in plastic bags and kept at about 4°–5° C. However, blood transfusions can only be performed with prewarmed blood, which is adapted to the body temperature and is warmed to, for example, 27° or even 33° C.

German Auslegeschrift No. 2,320,440 and German Offenlegungsschrift No. 2,418,155 disclose microwave appliances of this type for warming blood, in which appliances the blood is subjected to the warming process in bottles or even in bags. The retaining apparatus for the blood container consists of two half-shell-shaped jaws which can be clamped together, so that even a flat bag can be pressed by these half-shells more or less into cylindrical shape for exposure to the microwaves. This leads to the formation of different layer thicknesses as a consequence of uneven warming of the blood, which then has to be compensated by thorough mixing of the blood. However, since the axis of the retaining apparatus is arranged transversely, i.e. perpendicularly to the axis of rotation of the drive motor, only comparatively limited mixing of the liquid content takes place. Such bottles or cylindrical containers usually possess no nozzles or tubular extensions, so that the problem of warming the liquid with particularly small layer thicknesses does not occur.

Swiss Patent Specification No. 444,338 discloses a microwave appliance of another structural type, in which the axis of rotation of the drive and the axis of the bottle-shaped container are mutually aligned. These axes are arranged obliquely to the horizontal so that in the case of a rotary movement it is virtually only the wall of the container which is rotated relative to the liquid content. The motor can be driven to rotate or to reciprocate. A tumbling movement is also supposedly possible, without its being possible to recognize how this could be achieved.

SUMMARY OF THE INVENTION

The object of the present invention is to provide an apparatus of the type initially described, by means of which, in a very short period, only the amount of blood actually needed can be warmed, without impairing the blood by uneven warming, particularly local overheating. It is of course intended here that the warming should take place in a very short time and with particularly intensive mixing or swirling of the liquid in the bag.

This is achieved, according to the invention, in that the axis of the receiving apparatus is arranged obliquely to the axis of rotation of the electric motor, and in that the receiving apparatus possesses a clamping plate for receiving the bag. This permits rapid and intensive warming and mixing without the use of an additional disposable material. For the heating of a bag having a capacity of 400 to 500 ml from 4° C. to 32° C., a heating time of about 110 seconds is needed. This short time is always sufficient for the short-term warming merely of the blood immediately required. Storing warm blood is therefore no longer necessary. An essential feature of the invention is that the axis of the receiving apparatus is arranged not only transversely but obliquely to the axis of rotation of the electric motor, and that the receiving apparatus possesses a clamping plate, in other words a substantially plane surface, for receiving the bag. This in fact makes it possible to receive the bag on the clamping plate in a flat and substantially stretched position, and, in combination with the reversible drive by the electric motor, to impart to the said bag a particular oblique tumbling movement, which entails particularly intensive mixing and swirling of the blood to be warmed during the warming process. Not only is the individual blood particle accelerated or slowed differently in accordance with its differing distance from the axis of rotation; in addition, the accelerating and slowing forces are to be considered in combination with oblique surfaces of the bag wall, so that the direction of movement of the individual blood particles is changed at these oblique surfaces, this movement exhibiting a component extending towards the axis of rotation or parallel thereto. The force of gravity, of course, also acts on each individual particle. As a result of the influence of these three components, the particular oblique tumbling movement takes place in the form of intensive mixing, so that the content of the bag is warmed not only rapidly but also uniformly over the bag cross section. Since the apparatus is in use only for a brief period, it is quickly available for further supplies of stored blood, so that even a plurality of operating theatres can be serviced with one apparatus according to the invention. Moreover, no sterilization problems arise, since the blood remains, during warming, in the bag in which it is also stored.

The clamping plate can be arranged obliquely at an angle of about 45° to the horizontal, the drive for the rotary movement advantageously possessing an electric motor, which is reversibly controlled. Constant circulation and uniform warming of the blood takes place as a result of this pushing/turning movement of the bag. This type of reversible drive is particularly suitable for uniform mixing.

The electric motor can be controlled to pivot reciprocally within an angle of about 350°. This angular range has proved particularly advantageous in combination with a receiving plate arranged obliquely at an angle of 45°. It is also logical for the clamping plate to consist of a material which is warmed as little as possible, if at all, by means of microwaves, particularly plastic, so that only the blood and not the clamping plate is actually warmed up.

Consequently it is also impossible for any after-heating phenomena to take place between the clamping plate and the blood, since the clamping plate is simultaneously warmed as little as possible, if at all.

The clamping plate is advantageously provided with a fixing belt, a clamp clip, or the like, for fixing the bag, so that the preserved blood can be quickly and easily fixed to the oblique clamping plate.

A thermoelement for controlling the generator of the microwaves can be provided in the surface of the clamping plate which faces the bag. This thermoelement indicates the temperature, this temperature being measured as close as possible to the bag or the blood and not being, for example, the temperature of the clamping plate. The warming-up temperature for the blood can be set, via a suitable control device, according to requirements, for example at 27° C. or even at 33° C., to name some preferred warming-up temperatures.

A particularly advantageously equipped development, according to the invention, of the receiving apparatus is obtained when the receiving apparatus possesses a cover plate, the bag being retained and pressed flat in the sense of uniform layer thicknesses between this cover plate and the receiving plate, and if the receiving plate and the cover plate are coated, over a portion of their longitudinal and transverse extent corresponding to the arrangement of nozzles on the bag, with a material which reflects the microwaves. In this case, too, the axis of the receiving apparatus or of the clamping plate is arranged obliquely to the axis of rotation of the electric motor, in other words at an angle other than 90°. A cover plate is, however, now added to the clamping plate, this cover plate naturally likewise being designed as a plane surface and also being of comparable order of magnitude to the clamping plate. The bag is retained and pressed flat in the receiving apparatus between these two flat plates, so that the upward curves of the pliable bag are eliminated not only on one side but now on both sides, and moreover a chamber formation caused by the clamping belt without cover plate is eliminated. To the contrary, the layer thickness of the bag is constant over virtually the entire bag surface, since in the retaining position on the bag, the cover plate comes to rest aligned precisely or at least approximately parallel to the clamping plate. The equal layer thickness of the liquid in the bag guarantees not only a uniform warming over the surface, but there is also no further constriction at this cross section, so that the change in the direction of movement of the individual blood particles can exert its full effect according to a force component which acts in the direction of the axis of rotation, and hence the special oblique/tumbling mixture of the liquid in the bag arises unimpeded. The essential content of the bag is involved in this oblique/tumbling movement, but the portions of the liquid which are present in nozzles, tubular extensions or the like provided on the bag participate only partially, if at all, in this tumbling and mixing movement. Since however the layer thickness in a nozzle of this type is substantially reduced by comparison with the remaining layer thickness of the bag, both the clamping plate and cover plate are covered or provided with reflecting material within this area determined on the bag by the nozzles and tubular extensions, so that at least some of the microwaves are kept away, by reflection, from this region of the bag and from the liquid located therein. Since the clamping plate and the cover plate are located at a distance apart, some of the microwaves may nevertheless act on the liquid in the nozzles, through the gap formed, so that a relatively slower warming takes place here. This slower warming is entirely desirable, in order in all cases to avoid overheating phenomena in the sensitive liquid. The excellent mixing of the liquid resulting from the oblique/tumbling movement also takes effect up to the top edge of the bag, that is to say into a region which is partly screened by the reflecting material. For this reason it will be impossible for a temperature difference to build up here. It is only the small residual volume which is directly enclosed in the nozzles or tubular extensions of the bag which does not reach the final temperature during the warming process. This small residual volume is, however, negligible. The formation of clots in the blood or coagulation residues of the blood plasma is at any rate reliably avoided, the essential content of the bag also being warmed rapidly and uniformly. Since the position of the nozzles and tubular extensions on the bag cannot always be precisely foreseen, as the bags are also produced in quite a different manner, the dimensions selected for the region of screening must be sufficiently big, but as a consequence of the oblique/tumbling mixing this is not really a disadvantage.

The clamping plate and the cover plate advantageously possess, on their mutually facing sides, the reflecting material, which is generally a metal, a metal foil or a metal plate. When the bag is laid on the clamping plate, the reflecting material visible there forms an area which enables the bag to be so positioned, relative to the clamping plate, that the nozzles and tubular sections which are at risk come to rest within this area. An equal area of the bag is then screeningly protected by the cover plate from the other side.

The clamping plate and the cover plate consist, as a general rule, of plastic, since this is largely permeable to microwaves. The two plates may each be provided with a brass plate, depending on the arrangement of nozzles on the bag.

The brass plates may be arranged on the side of the clamping plate and of the cover plate which faces away from the axis of rotation of the electric motor, and may extend over one-third of the length of the clamping plate and of the cover plate. This is beneficial for easy and safe operation. The electric motor of the rotary drive advantageously remains constantly in the same relative position of the clamping plate to the horizontal in which the bag is clamped on or unclamped.

The arrangement of the cover plate relative to the clamping plate, in other words their articulated connection one to another and their pivoting or fixing movement, can be implemented in a quite different manner. The only really important thing is that the cover plate is fixed, in the clamping position, approximately parallel to the clamping plate, and that a certain pressure arises between the plates between which the bag is held and pressed flat. As bags of different sizes exist, it is advantageous that the cover plate can possess a perforation, through which a clamping belt is displaceably passed, the free end of the said belt being detachably connected to the clamping plate. This enables a certain alignment of the cover plate in its parallelism to the clamping plate to be achieved, which takes effect even with different bag capacities or permits a corresponding alignment.

BRIEF DESCRIPTION OF THE DRAWING

The invention is further described with reference to preferred exemplary embodiments. In the drawings.

DETAILED DESCRIPTION

Figure 1:
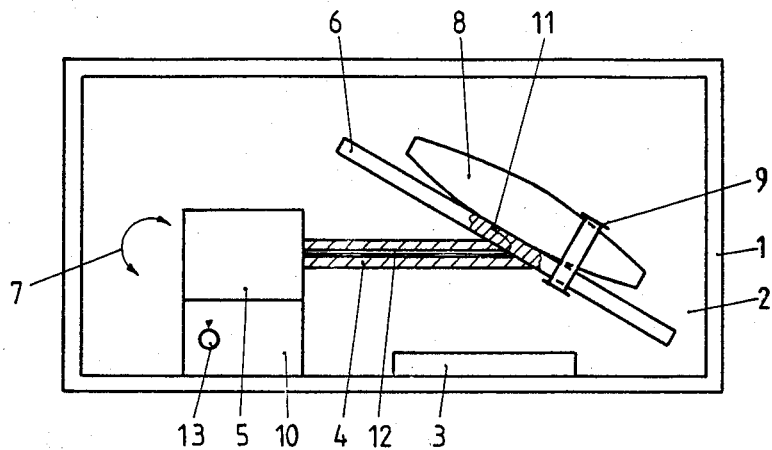
FIG. 1 shows a diagrammatic representation of the microwave appliance in a first embodiment.
Figure 2:
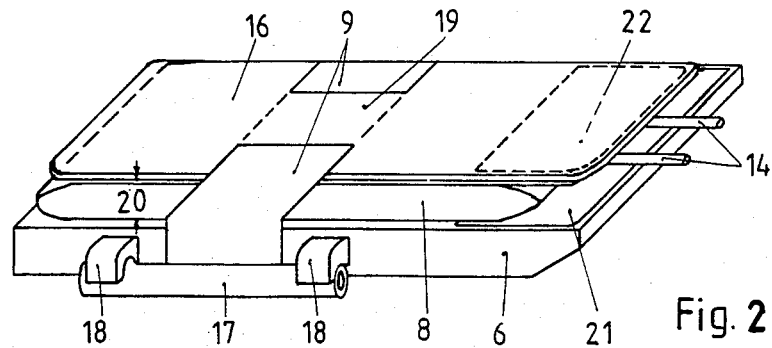
FIG. 2 shows a perspective view of those parts of the retaining apparatus of the microwave appliance which are essential for the invention, in a second embodiment.
Figure 3:
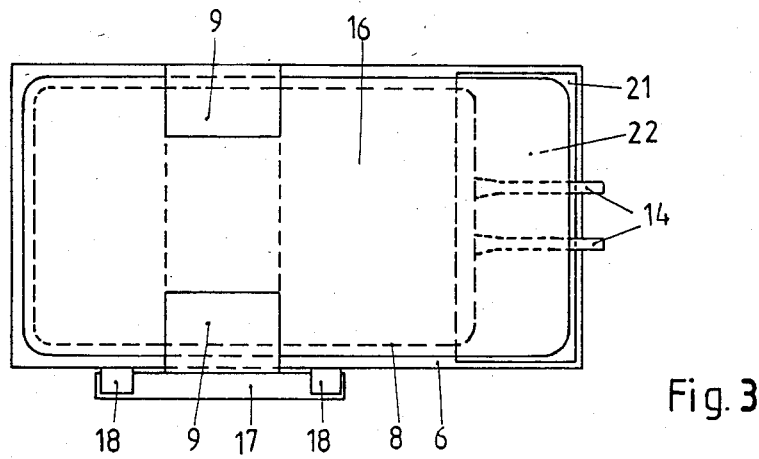
FIG. 3 shows a plan view of the parts according to FIG. 2 from above and, FIG. 4 shows a lateral view of the parts according to FIG. 2.

In a housing (1) which is merely indicated in FIG. 1, and is equipped with a door or another closure device, an inner chamber (2) is formed in which a generator (3) for microwaves is attached, as for example in a microwave oven. A shaft (4) is also rotatably mounted in the inner chamber (2), and is driven by an electric motor (5)

to pivot reciprocally. A clamping plate (6) is obliquely arranged at the free end of the shaft (4), and in its aligned central position encloses an angle of approximately 45° with the horizontal. The clamping plate (6) is thus arranged to be reciprocally pivotable, via the electric motor (5), through a pivoting angle of about 350° according to the arrow (7). The clamping plate (6) consists of plastic, which is warmed as little as possible, if at all, as a result of the microwaves of the generator (3). The clamping plate (6) serves to receive a bag (8) of the blood or blood derivative which is to be warmed. By means of a clamping device, clamp clip or the like (9) arranged on the clamping plate (6), the bag (8) is fixed on the clamping plate (6). Moreover, a control device (10) is arranged in the inner chamber (2). The temperature of the bag (8) or of the blood located therein is measured via a thermoelement (11) in the surface of the clamping plate (6) which faces the bag (8). From the thermoelement (11) a line (12) leads to the control device (10) which controls the generator (3) of the microwaves. By means of a setting button (13) the desired final temperature of the blood after heating can be determined. This temperature is normally 27°, but can also be set to other figures, e.g. 33° C. The time taken to heat up preserved blood, in a bag of 400 to 500 ml capacity, from 4° C. to 32° C. is about 110 seconds. As a result of the reciprocal, reversible drive of the clamping plate (6) by means of the motor (5), the bag (8) is caused to undergo a helical rotary movement during warming, as a result of which particularly good mixing of the blood takes place, so that all the blood located in the bag (8) is uniformly warmed.

Figure 4:
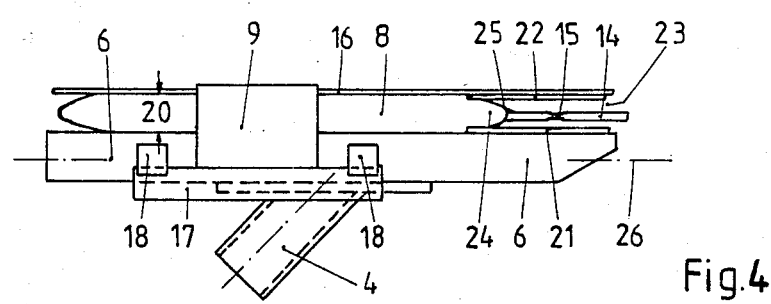

The bag (8), which usually consists of plastic film, receives the liquid to be warmed, namely the blood or the blood derivatives. The bag (8) is of approximately rectangular, flat shape and usually bears a plurality of nozzles (14) or other tubular extensions along its upper edge, these being used as filling or withdrawal apertures or serving other purposes. In FIG. 4 the closure (15) is shown on the nozzle (14), so that the liquid in the bag (8) rises as far as this closure (15).

The retaining apparatus for the bag possesses a clamping plate (6), which thus possesses a flat surface on which the bag (8) rests. A cover plate (16) is provided, parallel to the clamping plate but at a distance therefrom, this cover plate possessing a similar surface area to the clamping plate (6) and likewise, of course, being designed as a flat area. A clamping belt (9) is attached by one end to the clamping plate (6), and can be detachably suspended by its other end, with the aid of a toggle (17) arranged there, in two hooks (18). The clamping belt (4) passes through a perforation (19) on the cover plate (16). The clamping belt (9) consists of elastically pliable material, so that the cover plate (16) can be so aligned relative to the clamping belt (9), and fixed in the clamping position, that the cover plate (16) is located as nearly as possible exactly parallel to and at a distance from the clamping plate (6). The bag (8) is thus pressed flat and retained, over its substantial surface area, with a constant layer thickness (20) in the retaining apparatus.

In the upper region of the bag (8), where the nozzles (14) are provided or the top edge of the bag is located, the clamping plate (6) and the cover plate (16) are provided on their mutually facing surfaces with two brass plates (21 and 22) or are otherwise coated with a material which reflects the microwaves. The arrangement of the brass plates (21 and 22), i.e. their superficial extent and their positioning within the clamping plate (6) and the cover plate (16) are so selected that the top edge of the bag (8), including the part of the nozzles which leads to the closure (15), are in all cases situated within the outline of the brass plates (21 and 22). These brass plates (21 and 22) protect those parts of the bag or of the nozzles (14) which are located in the field between them from the excessive action of microwaves. Obviously, microwaves can penetrate laterally through the gap (23) formed between the brass plates (21 and 22), these microwaves desirably leading to a relatively slower, and hence lower-temperature, warming of the liquid in the nozzle (14) as far as the closure (15). Although the liquid at the point (24), in other words approximately along the top edge (25) of the bag (8), is also partly screened by the brass plates (21 and 22), this point (24) nevertheless participates in the special oblique/tumbling mixing of the main content of the bag (8), so that no temperature differences from the remaining content of the bag can form here.

FIG. 4 also shows the relative position between the rotating shaft (4) and the axis (26) of the clamping plate (6) or of the entire retaining apparatus. These axes (4 and 26) are mutually oblique, in other words arranged at an angle other than 90°. The extension of the shaft (4) or of the corresponding shaft stub leads to or corresponds to the axis of the electric motor for the rotary drive. The shaft (4) can preferably be arranged with a horizontal alignment, so that the axis (26) is finally arranged obliquely to the horizontal at the microwave appliance, in other words at an angle to the horizontal of 90°.

I claim:

1. A microwave appliance for warming blood and the like stored in a bag, said appliance including a housing defining a warming chamber, a microwave generator for generating microwaves in said warming chamber, a bag support member with a substantially flat surface for supporting the bag filled with blood, a clamp member for clamping the bag to the flat surface of said bag support member, a shaft member mounted at one of its end portions to said bag support member and having a longitudinal axis extending at an oblique angle with respect to the flat surface of said bag support member, a reversible motor for oscillating said bag support member, the other end portion of said shaft member being mounted to and oscillated about its longitudinal axis by said reversible motor, whereby the flat surface of said bag support member and the bag filled with blood and clamped to the flat surface oscillate about the longitudinal axis of said shaft member with a wobbling motion.

2. The microwave appliance as claimed in claim 1 wherein a thermoelement for controlling said microwave generator is provided in the surface of said bag support member which faces the bag.

3. The microwave appliance of claim 1 and wherein the longitudinal axis of said shaft member is approximately horizontal, and the substantially flat surface of said bag support member is oriented at an approximately 45° angle with respect to the longitudinal axis of said shaft member.

4. The microwave appliance of claim 1 and wherein said clamp member for clamping the bag to the flat surface of said bag support member comprises a belt attached to said bag support member for holding the bag against the flat surface of said bag support member.

5. The microwave appliance of claim 1 and wherein said clamp member for clamping the bag to the flat surface of said bag support member comprises a cover plate having a substantially flat surface for engagement with the bag to press the bag in a flattened shape of approximately uniform thickness against the flat surface of said bag support member.

6. The microwave appliance of claim 5 and wherein said bag support member and said cover plate include overlying portion coated with a material which reflects mirowaves so that a portion of the bag can be placed between the overlying coated portions and shielded from the microwaves.

7. The microwave appliance of claim 1 and wherein said bag support member and said clamp member comprise separable plate members with substantially flat facing surfaces normally positioned in overlying parallel relationship when engaging the bag, said plate members including at their end portions positioned away from said motor overlying brass plates which extend over about one third of the lengths of the plate members for shielding a portion of the bag from microwaves.

8. A microwave appliance for warming blood and the like stored in a flexible bag comprising a housing defining a warming chamber, a microwave generator for generating microwaves in said warming chamber, a shaft member positioned in said warming chamber with its longitudinal axis extending approximately horizontally in said warming chamber, a reversible motor connected in driving relationship with one end portion of said shaft member and arranged to oscillate said shaft member about its longitudinal axis, a bag support assembly mounted to the other end portion of said shaft member, said bag support assembly including a substantially flat bag support surface and means for holding a bag filled with blood against said bag support surface, said bag support surface oriented at an oblique angle with respect to the longitudinal axis of said shaft member and the axis of said shaft extending through said bag support surface whereby the oscillation of the shaft by the motor results in the bag filled with blood oscillating with a wobbling movement.

* * * * *